(12) United States Patent
Badiey et al.

(10) Patent No.: US 8,886,498 B2
(45) Date of Patent: Nov. 11, 2014

(54) SIMULATOR AND METHOD FOR SIMULATING AN ACOUSTIC FIELD OF AN ACOUSTIC WAVEGUIDE

(75) Inventors: Mohsen Badiey, Newark, DE (US); Boris G. Katsnelson, Voronezh (RU)

(73) Assignee: University of Delaware, Newark, DE (US)

( * ) Notice: Subject to any disclaimer, the term of this patent is extended or adjusted under 35 U.S.C. 154(b) by 351 days.

(21) Appl. No.: 13/310,095

(22) Filed: Dec. 2, 2011

(65) Prior Publication Data

US 2012/0197604 A1 Aug. 2, 2012

Related U.S. Application Data

(60) Provisional application No. 61/419,484, filed on Dec. 3, 2010.

(51) Int. Cl.
| | |
|---|---|
| *G01V 1/30* | (2006.01) |
| *G01N 29/02* | (2006.01) |
| *G01N 29/44* | (2006.01) |
| *G06F 17/50* | (2006.01) |
| *G01V 1/28* | (2006.01) |
| *G01S 15/89* | (2006.01) |
| *G01N 29/024* | (2006.01) |

(52) U.S. Cl.
CPC ...... *G06F 17/5009* (2013.01); *G01V 2210/675* (2013.01); *G01N 29/024* (2013.01); *G06F 2217/16* (2013.01); *G01V 1/282* (2013.01); *G01N 29/02* (2013.01); *G01S 15/89* (2013.01); *G01V 2210/671* (2013.01); *G01N 29/4472* (2013.01); *G01V 1/303* (2013.01)
USPC ............ 703/2; 702/18; 367/93; 703/9

(58) Field of Classification Search
CPC ......... G01V 1/282; G01V 1/30; G01V 1/303; G01V 1/306; G01V 1/308; G01V 2210/67; G01V 2210/671; G01N 29/024; G01N 29/4472; G01N 29/032; G01N 29/44; G01N 29/4418; G01S 17/02; G06F 17/5009; G06F 2217/16
USPC ............ 703/2, 5, 9, 10; 367/8, 10, 92, 25–35, 367/83; 702/14, 18; 166/66
See application file for complete search history.

(56) References Cited

U.S. PATENT DOCUMENTS

| | | | |
|---|---|---|---|
| 5,466,157 | A | 11/1995 | Henderson et al. |
| 7,499,837 | B2 | 3/2009 | Szeto |

(Continued)

OTHER PUBLICATIONS

Kuz'kin, V.M., et al. "Method for Measuring the Frequency Shifts of Interference Maxima in Monitoring of Dispersion Media: Theory, Implementation, and Prospects" Physics of Wave Phenomena, vol. 18, No. 3, pp. 196-222 (Sep. 2010).*

(Continued)

*Primary Examiner* — Kamini S Shah
*Assistant Examiner* — Jay B Hann
(74) *Attorney, Agent, or Firm* — RatnerPrestia (57) ABSTRACT

Simulators and methods for simulating an acoustic field of an acoustic waveguide are provided. A sound speed profile of the acoustic waveguide is generated, where the acoustic waveguide has a region of a first fluid within a second fluid, and the first fluid has a different acoustic index of refraction than the second fluid. The sound speed profile and predetermined parameters of a sound source and a receiver are applied to a parabolic equation (PE) model of sound propagation in the acoustic waveguide. The acoustic field of the acoustic waveguide is determined from the PE model. The acoustic field includes an interference pattern from interference between an acoustic signal of the acoustic source and at least one signal refracted by the region of the second fluid.

22 Claims, 8 Drawing Sheets
(3 of 8 Drawing Sheet(s) Filed in Color)

(56) References Cited

U.S. PATENT DOCUMENTS

| | | | |
|---|---|---|---|
| 7,606,113 B2 * | 10/2009 | Londo et al. ............. | 367/13 |
| 2005/0278158 A1 | 12/2005 | Ellison et al. | |
| 2006/0280030 A1 | 12/2006 | Makris et al. | |
| 2008/0239873 A1 | 10/2008 | Tsurugaya et al. | |
| 2009/0067290 A1 | 3/2009 | Londo et al. | |

OTHER PUBLICATIONS

Kuz'kin, V.M., & Pereselkov, S.A. "Reconstruction of Internal Waves in Oceanic Waveguides" Acoustical Physics, vol. 55, No. 3, pp. 406-410 (2009).*

Tielburger, Dirk, et al. "Acoustic Propagation Through an Internal Wave Field in a Shallow Water Waveguide" J. Acoust. Soc. Am., vol. 101, No. 2, pp. 789-808 (1997).*

Dajun & Henyey, Frank "Reverberation Clutter from Combined Internal Wave Refraction and Bottom Backscatter" J. Acoust. Soc. Am., vol. 127 (Mar. 2010) (Abstract only).*

Wilkin, John, et al. "4-Dimensional Variational Assimilation of Satellite Temperature and Sea Level Data in the Coastal Ocean and Adjacent Deep Sea" ROMS user meeting, Grenoble (2008).*

Apaydin, Gokhan & Sevgi, Levent "Split-Step-Fourier and Finite-Element-Based Parabolic-Equation Propagation-Prediction Tools: Canonical Tests, Systematic Comparisons, and Calibration" IEEE Antennas & Propagation Magazine, vol. 52, No. 3 (Jun. 2010).*

Badiey et al., "Acoustic multipath arrivals in the horizontal plane due to approaching nonlinear internal waves", J. Acoust. Soc. Am 129 (4), Apr. 2011.

Toner et al., "Chlorophyll Dispersal by Eddy-Eddy Interactions in the Gulf of Mexico", Journal of Geophysical Research, vol. 108, No. C4, 3105, 2003.

Kuznetsov et al., "The Loop Current and adjacent rings delineated by Lagrangian analysis of the near-surface flow", Journal of Marine Research, 60, pp. 405-429, 2002.

Makris et al., "Fish Population and Behavior Revealed by Instantaneous Continental Shelf-Scale Imaging", Science, vol. 311, pp. 660-663, Feb. 3, 2006.

Klemas, "Tracking Oil Slicks and Predicting their Trajectories Using Remote Sensors and Models: Case Studies of the Sea Princess and Deepwater Horizon Oil Spills", Journal of Coastal Research, vol. 26, No. 5, pp. 789-797, 2010.

Ball et al., "Phase behavior and physical properties of petroleum reservoir fluids from acoustic measurements", Journal of Petroleum Sciene and Engineering 34, pp. 1-11, 2002.

McCain, Jr., et al., "The Coefficient of Isothermal Compressibility of Black Oils at Presures Below the Bubblepoint", SPE Formation Evaluation, pp. 659-662, Sep. 1988.

Petrosky, Jr, et al., "Pressure-Volume-Temperature Correlations for Gulf of Mexico Crude Oils", Society of Petroleum Engineers, SPE 26644, pp. 395-406, 1993.

Wang, et al., "Acoustic Velocities in Petroleum Oils", JPT, Feb. 1990, pp. 192-200.

Written Opinion for International Application No. PCT/US2011/063062, dated Oct. 23, 2012.

International Preliminary Report on Patentability for International Application No. PCT/US2011/063062, dated Jun. 4, 2013.

International Search Report for International Appln. No. PCT/US2011/063062, dated Oct. 23, 2012.

* cited by examiner

SIMULATOR AND METHOD FOR SIMULATING AN ACOUSTIC FIELD OF AN ACOUSTIC WAVEGUIDE

CROSS REFERENCE TO RELATED APPLICATIONS

This application claims priority to U.S. Provisional Application Ser. No. 61/419,484, entitled "UNDERWATER ACOUSTIC REFRACTO-INTERFEROMETER," filed Dec. 3, 2010, incorporated fully herein by reference.

STATEMENT REGARDING FEDERALLY SPONSORED RESEARCH

The present invention was supported in part by Grant Number N000141010396 from the Office of Naval Research. The United States Government may have certain rights to the invention.

FIELD OF THE INVENTION

The present invention relates to the field of sound propagation modeling and, more particularly, to methods and systems for simulating an acoustic field of an acoustic waveguide having a region of a first fluid within a second fluid.

BACKGROUND OF THE INVENTION

Shallow water environments typically induce variability on acoustic wave propagation due to their inhomogeneous nature. For example, acoustic signals can be refracted (or reflected) from various boundaries including the sea surface and the sea bottom. Acoustic signals can also be refracted (reflected) within the water column itself, such as from temperature fronts and internal waves. Internal waves, for example, can produce large fluctuations on shallow water acoustic signals, both in amplitude and phase. These fluctuations may affect underwater array processing results, such as for source localization and inverse problem (medium) studies.

In general, internal waves are gravity waves that may oscillate within a fluid medium. (Nonlinear solitary internal waves are typically referred to as solitons.) For example, an internal wave may propagate along the boundary between low and high density water regions. Internal waves may propagate vertically as well as horizontally.

It is desirable to model the effects of fluctuations, such as internal waves, in the water column.

SUMMARY OF THE INVENTION

The present invention is embodied in a method for simulating an acoustic field of an acoustic waveguide. A sound speed profile of the acoustic waveguide is generated by a processor. The acoustic waveguide has a region of a first fluid within a second fluid and the first fluid has a different acoustic index of refraction than the second fluid. The sound speed profile and predetermined parameters of a sound source and a receiver are applied to a parabolic equation (PE) model of sound propagation in the acoustic waveguide. The acoustic field of the acoustic waveguide is determined by the process or from the PE model. The acoustic field includes an interference pattern from interference between an acoustic signal of the acoustic source and at least one signal refracted by the region of the second fluid.

The present invention is further embodied in a simulator for simulating an acoustic field of an acoustic waveguide. The simulator includes a sound speed profile generator and an acoustic field generator. The sound speed profile generator is configured to generate a sound speed profile of the acoustic waveguide, where the acoustic waveguide has a region of a first fluid within a second fluid and the first fluid has a different acoustic index of refraction than the second fluid. The acoustic field generator is configured to: apply the sound speed profile and predetermined parameters of a sound source and a receiver to a parabolic equation (PE) model of sound propagation in the acoustic waveguide, and determine the acoustic field of the acoustic waveguide from the PE model. The acoustic field includes an interference pattern from interference between an acoustic signal of the acoustic source and at least one signal refracted by the region of the second fluid.

Systems and methods of the present invention may be used, for example, by the navy, for oil exploration, for oceanography, etc.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention may be understood from the following detailed description when read in connection with the accompanying drawing. It is emphasized that, according to common practice, various features of the drawing may not be drawn to scale. On the contrary, the dimensions of the various features may be arbitrarily expanded or reduced for clarity. Moreover, in the drawing, common numerical references are used to represent like features. Included in the drawing are the following figures.

DETAILED DESCRIPTION OF THE INVENTION

According to aspects of the present invention, propagation of acoustic waves can be used to map a three-dimensional (3D) structure of a water column with a horizontal scale of about a few tens of kilometers. If the water column has a patch of oil intrusion, because of the vast contrast between the sound properties of the oil and water (sound speed in oil is about 1300-1350 m/s), the index of refraction in the water column may be changed. This change may be measured by acoustical sounding using source and vertical and/or horizontal hydrophone receiving arrays and a 3D structure of the water column may be constructed. To map the contours of oil patches and layers inside the water column in the horizontal plane and its behavior in space and time, a variation of interference pattern in the horizontal plane may be utilized. These interference patterns may be produced in an area of multipath propagation of sound rays due to horizontal refraction. According to an exemplary embodiment of the present invention, an acoustic field simulator may be used for estimation of position and velocity of a boundary of a 3D structure with a sound speed distinct from the surrounding fluid (such as temperature front, internal waves, oil spill, etc.), using measurement of the horizontal interference structure. According to aspects of the present invention, sound signals of different frequencies (from 50 Hz to a few kilohertz) may provide enough accuracy for mapping of similar inclusions.

Aspects of the invention include simulators and methods for simulating an acoustic field of an acoustic waveguide. An exemplary method includes generating a sound speed profile of the acoustic waveguide, where the acoustic waveguide includes a region of a first fluid within a second fluid, and the first fluid has a different index of refraction than the second fluid. The sound speed profile and predetermined parameters of a sound source and a receiver may be applied to a parabolic equation (PE) model of sound propagation in the acoustic waveguide. The acoustic field of the acoustic waveguide for the sound source and the receiver may be determined from the PE model. According to an exemplary embodiment of the present invention, the acoustic field includes an interference pattern from interference between an acoustic signal of the acoustic source and at least one signal refracted by the region of the second fluid.

Interferometry techniques are known in optics. In particular, the Lloyd's mirror effect is known in optics, and relates to the detection of interfering rays due to an approaching layer having different optical refraction properties. According to aspects of the present invention, acoustic ray interference in the horizontal direction may be simulated, due to a moving region with a different sound index of refraction from the surrounding fluid.

An exemplary function of the invention is to be able to model and change in time, the boundary of a fluid that possesses an acoustic index of refraction different from the surrounding fluid.

Aspects of the present invention have been shown analytically, and also by using an acoustic propagation model (e.g., a PE model). Initial modeling results using a PE model show that when a submerged fluid (i.e., a region of fluid) with a different index of refraction is placed within another fluid, and an acoustic field impinges upon it, refraction and interference patterns around and within the region are generated.

A shallow water acoustic experiment was previously conducted, where a sound source transmitted pulses about 20 kilometers away from an L-shaped receiver array. The experiment and results are described in a related patent application entitled "METHOD FOR DETECTION OF A PLUME OF A FIRST FLUID WITHIN A SECOND FLUID," U.S. patent application Ser. No. 13/273,852 filed on Oct. 14, 2011, incorporated herein by reference in its entirety. The fringe patterns of the sound measurements at the receiver showed the existence of an interference pattern phenomenon similar to the Lloyd's mirror effect, indicating that it is possible to measure horizontal refraction in an oceanic waveguide.

Aspects of the present invention include a modeling tool (i.e., a simulator) to simulate the motion of a region of a first fluid released within a three-dimensional (3D) waveguide filled with a second fluid, where the physical properties of the second fluid are different from the first fluid. An exemplary simulator may be used to design numerical experiments prior to investment of costly field exploration (such as in case of natural or man-made disasters).

Figure 1:
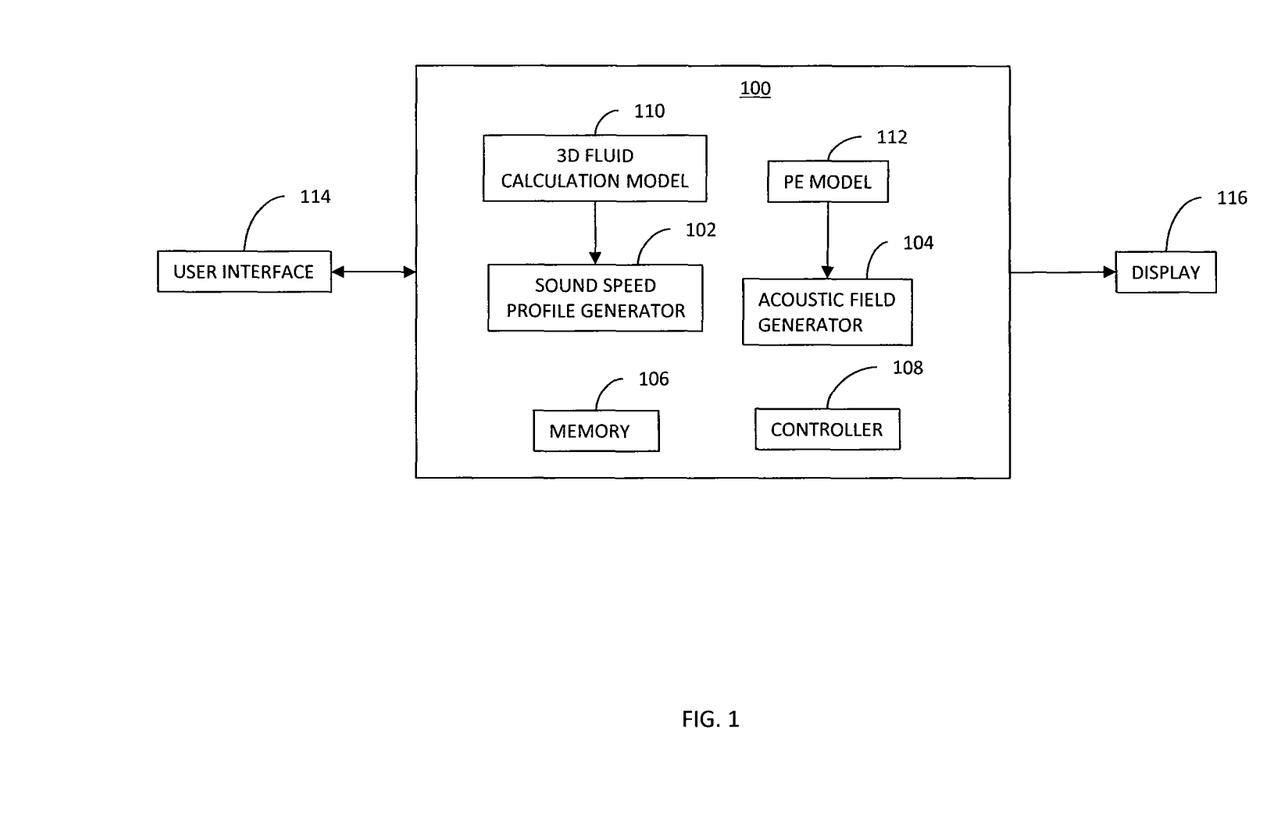
FIG. 1 is a functional block diagram of an exemplary acoustic field simulator, according to aspects of the present invention.

Referring to FIG. 1, a functional block diagram of an exemplary acoustic field simulator, designated generally as simulator 100, is shown. Simulator 100 may include sound speed profile generator 102, acoustic field generator 104, memory 106, controller 108, 3D fluid calculation model 110 and PE model 112. Simulator 100 may be coupled to user interface 114 and display 116. Although user interface 114 and display 116 are illustrated as being external to simulator 100, one or more of user interface 114 and display 116 may be included as part of simulator 100. Although not shown, simulator 100 may be coupled to a remote location, for example via a global network (i.e., the Internet).

Sound speed profile generator 102 may be configured to generate a sound speed profile of an underwater channel (for example, underwater channel 200 shown in FIGS. 2A and 2B) having a region of fluid with an index of refraction that is different from the underwater channel. The sound speed profile may be generated based on an output of 3D fluid calculation model 110. 3D fluid calculation model 110 may calculate a fluid dynamic Lagrangian method, to track particle trajectories inside the region of fluid (for example fluid 204 of region 202 shown in FIG. 2A) and to provide input to an acoustic model of the underwater channel. In an exemplary embodiment, 3D fluid calculation model 110 may use a combination of a regional ocean modeling system (ROMS) and Lagrangian method. The ROMS component may be used to model a background environment of the underwater channel (for example, underwater channel 200 shown in FIG. 2A). Sound speed profile generator 102 is described further below with respect to FIGS. 5, 6A and 6B.

Figure 2A:
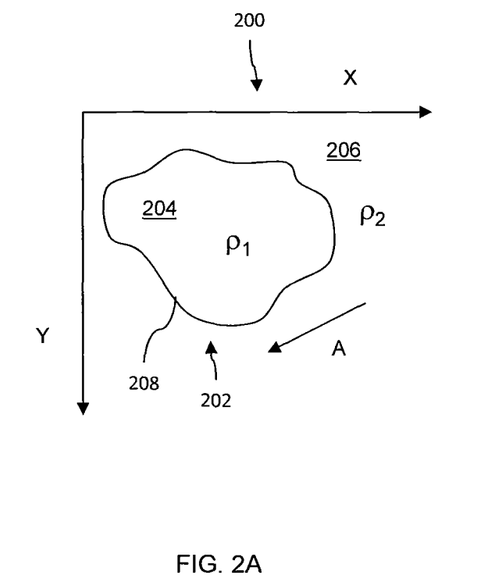
FIG. 2A is a top plan view diagram of an exemplary underwater channel having a region of fluid moving in the horizontal plane, according to an aspect of the present invention.
Figure 4:
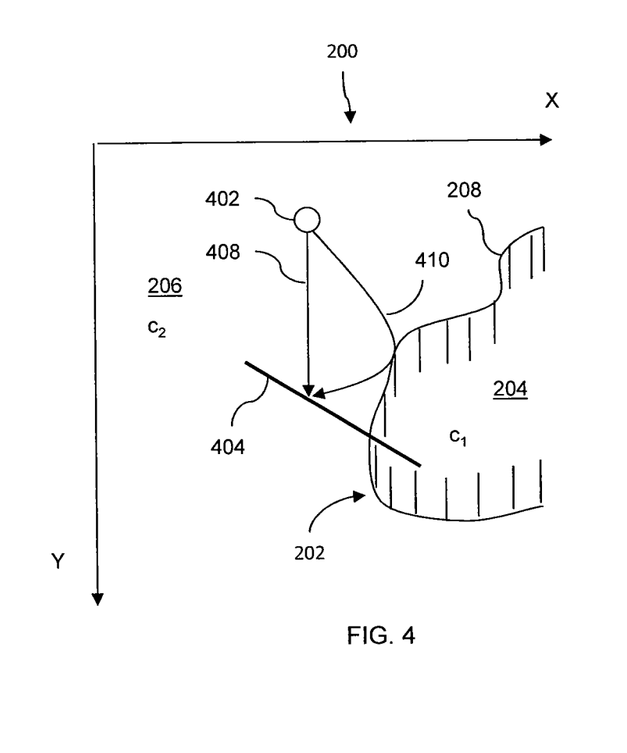
FIG. 4 is a top view diagram of an exemplary underwater channel having a region of fluid within the underwater channel, illustrating the behavior of acoustic rays in horizontal plane (X-Y) in a vicinity of a region fluid with different sound index of refraction, according to an aspect of the present invention.

Acoustic field generator 104 may be configured to receive the sound speed profile from sound speed profile generator 102, as well as parameters associated with a sound source (for example, sound source 402 shown in FIG. 4) and a receiver (for example, receiver 404 shown in FIG. 4) positioned within the underwater channel. The sound speed profile and the parameters of the sound source and the receiver may be applied to PE model 112 for modeling sound propagation in the underwater channel. In an exemplary embodiment, PE model 112 includes a parallelized 3D PE model. According to another exemplary embodiment, PE model 112 may include a two-way PE model (i.e., to consider both forward and backward propagating waves). Although PE model 112 is described, any suitable acoustic propagation model may be used in place of PE model 112. For example, acoustic propagation models based on methods of Normal Modes or Ray Theory may be used. These Normal Modes and Ray Theory models, however, may not be as efficient as the PE model. Acoustic field generator 104 may generate an acoustic field based on the PE model (for example, for sound source 402 and receiver 404 as positioned in underwater channel 200, as shown in FIG. 4), that includes an interference pattern due to a region of fluid in the underwater channel (for example, region 202 of fluid 204 within fluid 206 of underwater channel 200, as shown in FIG. 2A). Acoustic field generator 104 is described further below with respect to FIG. 5.

Sound speed profile generator 102 and acoustic field generator 104 may be used to model changes in the region of fluid (for example, region 202 of fluid 206 as shown in FIG. 2A) over one or more geotimes. For example, region 202 (FIG. 2) may be modeled with a change in shape, position and/or physical characteristics with respect to different geotimes. A sound speed profile and acoustic field may be determined for each geotime (using sound speed profile generator 102 and acoustic field generator, respectively).

Memory 106 may be configured to store parameters associated with one or more of region 202 (FIG. 4) (i.e., the first fluid), fluid 206 of the underwater channel 200 (i.e., the second fluid), sound source 402 and receiver 404. Parameters of region 202 (FIG. 4) may include, for example, at least one of physical characteristics of fluid 204, a shape of region 202, or a position of region 202 in underwater channel 200. The physical characteristics, shape and/or position of the region 202 (FIG. 4) may also be stored according to one or more geotimes. The physical characteristics of the region 202 (FIG. 4) and fluid 206 of underwater channel 200 may include, for example, salinity, a viscosity or a temperature. Memory 106 may also store at least one of a sound speed profile, an acoustic field, parameters associated with 3D fluid calculation model 110 or parameters associated with PE model 112. Memory 106 may include, for example, a magnetic disk, an optical disk or a hard drive.

Controller 108 may be coupled to one or more of sound speed profile generator 102, acoustic field generator 104, memory 106, 3D fluid calculation model 110 and PE model 112, to control generation of an acoustic field. Controller 108 may include, for example, a logic circuit, a digital signal processor or a microprocessor. It is understood that one or more functions of sound speed profile generator 102 and/or acoustic field generator 104 may be performed by controller 108.

User interface 114 may include any suitable user interface capable of providing parameters associated with one or more of region 202 (FIG. 4), fluid 206 of underwater channel 200, sound source 402, receiver 404, sound speed profile generator 102, acoustic field generator 104, 3D fluid calculation model 110 and PE model 112. User interface 114 may include, for example, a pointing device, a keyboard and/or a display device.

Display 116 may include any suitable display device capable of presenting at least one of the sound speed profile and the acoustic field for one or more geotimes. Although user interface 114 and display device 116 are illustrated as separate devices, it is understood that the functions of user interface 114 and display device 116 may be combined into one device.

Suitable sound speed generator 102, acoustic field generator 104, memory 106, controller 108, 3D fluid calculation model 110, PE model 112, user interface 114 and display 116 may be understood by the skilled person from the description herein.

In general, simulator 102 may be considered to operate in two stages. Mathematical models of region 202 (FIG. 4) (such as an oil spill (i.e. an irregularly shaped fluid volume with boundary 208 changing in time and space)), underwater channel 200, sound source 402, and receiver 404 may be developed and stored (such as in memory 106).

In a first stage, simulator may prepare all of the parameters of the problem including the geometry and the physical parameters of the components (i.e. region 202 (FIG. 4), underwater channel 200, source 402 and receiver 404).

In the second stage two numerical models may be used. 3D fluid calculation model 110 may calculate the fluid dynamic Lagrangian method, to track particle trajectories inside a fluid volume of region 202 (FIG. 2A with density of $\rho_1$) and to provide input to the acoustic field generator 104 (and PE model 112). PE model 112 may be used to calculate the 3D acoustic field. A 3D PE numerical model may be used to obtain the acoustic field due to the interaction of sound with the fluid volume obtained in the previous calculations.

It is understood that acoustic field generator 104 may check the acoustic field for detection of recognizable acoustic interference patterns that result from the movement of region 202 (FIG. 4) of fluid 204 within fluid 206. If a prescribed convergence criterion is met, for example, if the pattern is associated with a known condition of the fluid temporal and spatial geometry, then the results will be passed on to the higher level (i.e., for visualization such as by display 116). Otherwise, the computation of the acoustic field may continue by acoustic field generator 104.

For any of the model runs there may be some possible variability, governed by a set of parameters. For example, if a model of an oil spill is considered to have a shape of an ellipse with semi-axes a, and b (such as region 602 shown in FIGS. 6A and 6B), a center of this ellipse may be placed at the point $(x_0, y_0)$, and other parameters such as the thickness and depth of the ellipse may also be considered. A model of the water column 600 (FIGS. 6A and 6B) may also include parameters, which may be changed, such as the depth H and the sound speed profile c(z) (for example, the sound speed profile may have a linear depth dependence: $c(z) = -z + c_0$ where $c_0$ is a background (reference) sound speed). A model of source 402 (FIG. 4) may include parameter depth $z_s$, and a model of receiver 404 may include a length L of an array of receiving elements, as well as the direction of the array.

In general, the above-described models may generate multiple results in which a variety of scenarios, such as different sound source and receiver positions and different background oceanographic conditions. Final results of these calculations may be stored in memory 106. Simulator 100 may use these data, for example, for visualization and demonstration purposes.

Figure 2B:
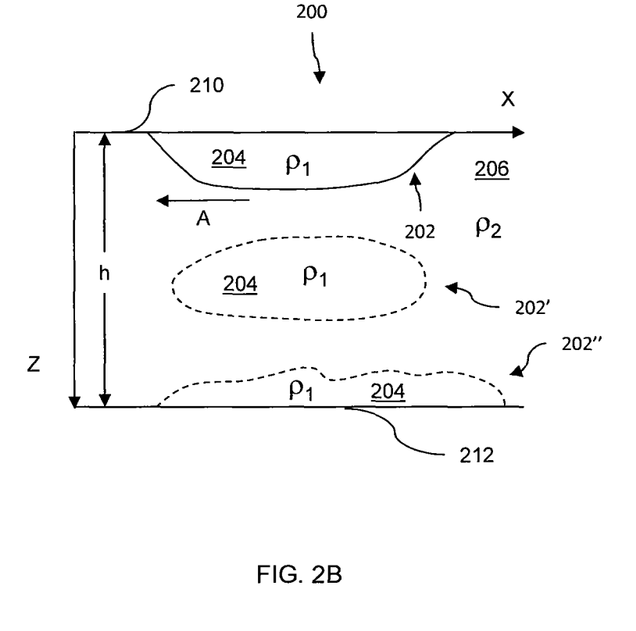
FIG. 2B is a side view diagram of the exemplary underwater channel shown in FIG. 2A, according to an aspect of the present invention.

Referring to FIGS. 2A and 2B, an exemplary underwater channel 200 having region 202 of fluid 204 (i.e., a first fluid) within fluid 206 (i.e., a second fluid) is described. In particular, FIG. 2A is a top plan view diagram of underwater channel 200, in the X-Y plane; and FIG. 2B is a side view diagram of underwater channel 200, in the X-Z plane. Underwater channel 200 includes top surface 210 and bottom surface 212, with a depth h therebetween. It is understood that region 202 represents a 3D volume of fluid 204.

As shown in FIG. 2A, underwater channel 200 may include region 202 of fluid 204 moving in a horizontal direction (i.e., the X-Y plane), designated generally by arrow A. Region 202 may have an irregularly shaped boundary 208.

Region 202 may include an internal wave (including nonlinear internal waves), a temperature front, or any oceanographic feature that may be moving within underwater channel 204 in the horizontal direction. In general region 202 of fluid 204 (i.e., a first fluid) represents any fluid having an acoustic index of refraction different from fluid 206 (i.e., a second fluid) of underwater channel 200. Fluid 206 may be, for example, for a shallow water region, for an underwater channel or for a water column. Although underwater channel 200 is described herein, it is understood that underwater channel 200 may represent any 3D acoustic waveguide.

Region of fluid 202 having density $\rho_1$ with soft (flexible) boundary 208 that is moving in fluid 206 of different density $\rho_2$ may be modeled, for example, using a Lagrangian formulation. In the X-Y plane (FIG. 2A), region 202 with irregular boundary 208 may move in any arbitrary direction.

Referring to FIG. 2B, in the vertical plane (i.e., the X-Z plane), region 202 may occupy a volume of underwater channel 200. Depending on densities $\rho_1$ and $\rho_2$, a region of fluid may occupy a volume of underwater channel 200 on top surface 210 (illustrated as region 202) (for $\rho_1 < \rho_2$), in a mid-portion of underwater channel 200 (illustrated as region 202') (for $\rho_1$ approximately equal to $\rho_2$) or near the bottom surface 212 (illustrated as region 202") (for $\rho_1 > \rho_2$). Accordingly, region 202 can float toward top surface 210, region 202' can float along in a mid-portion of underwater channel 200 or region 202" can sink toward bottom surface 210. Therefore, the physical properties of underwater channel 200 can change, causing the sound speed profile (C(z)) to change.

Figure 3:
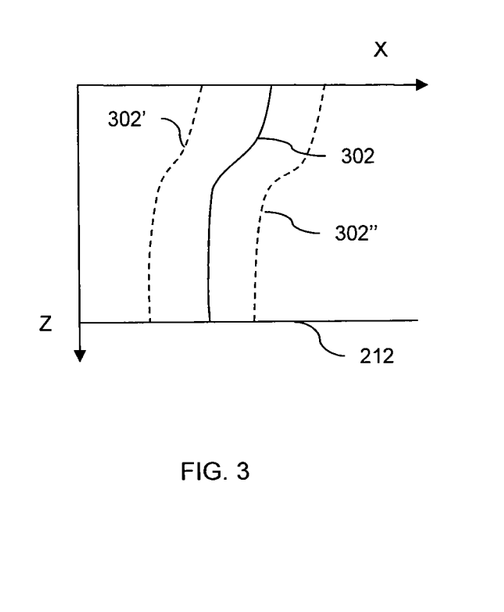
FIG. 3 is a graph of sound speed as a function of depth of an exemplary underwater channel illustrating changes to the sound speed due to a region of fluid within the underwater channel, according to an aspect of the present invention.

Referring to FIG. 3, a graph of example sound speed profile 302 as a function of depth (Z) is shown. Sound speed profile 302 illustrates a typical sound speed profile in shallow water. Sound speed profile 302 may vary (for example, as sound speed profile 302' or sound speed profile 302"). Variations in sound speed profile 302 may induce temporal and spatial variability of the acoustic field. For example, a moving region 202 of fluid 204 (FIG. 2A) with a different temperature than fluid 206 may refract (reflect) sound rays and may cause a multipath arrival that is detectable by a receiver.

In general, sound speed profile 302 may be a function of temperature, salinity and hydrostatic pressure. For a typical shallow water channel, hydrostatic pressure and salinity may provide a small contribution. Accordingly, sound speed profile 302 may be determined by the temperature of underwater channel 200 (FIG. 2A) (based on both fluid 204 and fluid 206) as a function of depth Z.

Referring to FIG. 4, a top view diagram of underwater channel 200 including a simulated sound source 402 and receiver 404 are shown. FIG. 4 illustrates the behavior of acoustic signals (also referred to herein as acoustic rays) 408 and 410 in a vicinity of region 202. Acoustic signal 408 represents the direct signal transmitted by sound source 402, which propagates through fluid 206 of underwater channel 200 (without being influenced by region 202). Acoustic signal 410 represents an acoustic signal transmitted by sound source 402 that is refracted (or reflected) at boundary 208 between region 202 and fluid 206. Interference between direct signal 408 and refracted signal 410 may produce an interference pattern, which may be detected by receiver 404. Both modal contents and horizontal ray contents of acoustic wave propagation may be affected by interaction with region 202, causing a received signal at receiver 404 to have a fluctuating intensity.

The problem of refraction of the acoustic field in the horizontal plane and multipath formation is similar to what occurs in optics where a light beam refracts due to the medium's variability in the light index of refraction, resulting in multipath arrivals of the refracted light beams. In the case of fluid 204 and fluid 206, the boundary 208 between the two fluids (fluid 204 and fluid 206) with different sound speeds $c_1$ (region 202 of fluid 204) and $c_2$ (fluid 206 of underwater channel 200), creates the necessary condition for the refraction of a sound beam. When two fluids are placed inside an acoustic field, under the right conditions, sound beam refraction can occur in the acoustic field and therefore the sound intensity due to interference between the direct arrival and the refracted arrival occurs.

In an exemplary embodiment, sound source 102 may be modeled to transmit acoustic signal 408 of low frequency (i.e., having a low frequency component). Acoustic signal 408 may be generally between about 50 Hz to a few kilohertz. Acoustic signal 408 may be a narrowband or a broadband signal. Acoustic signal 408 may include a plurality of pulses repeated periodically, such as a linear frequency modulated (LFM) signal (e.g., a chirp) or may include a continuous signal, such as a pseudorandom binary sequence (e.g., a maximum length sequence (MLS)).

Receiver 404 may include one or more receiving elements (not shown). A plurality of receiving elements may be arranged as a horizontal array, a vertical array or a combination of a vertical array and a horizontal array (i.e., an L-shaped array).

Figure 5:
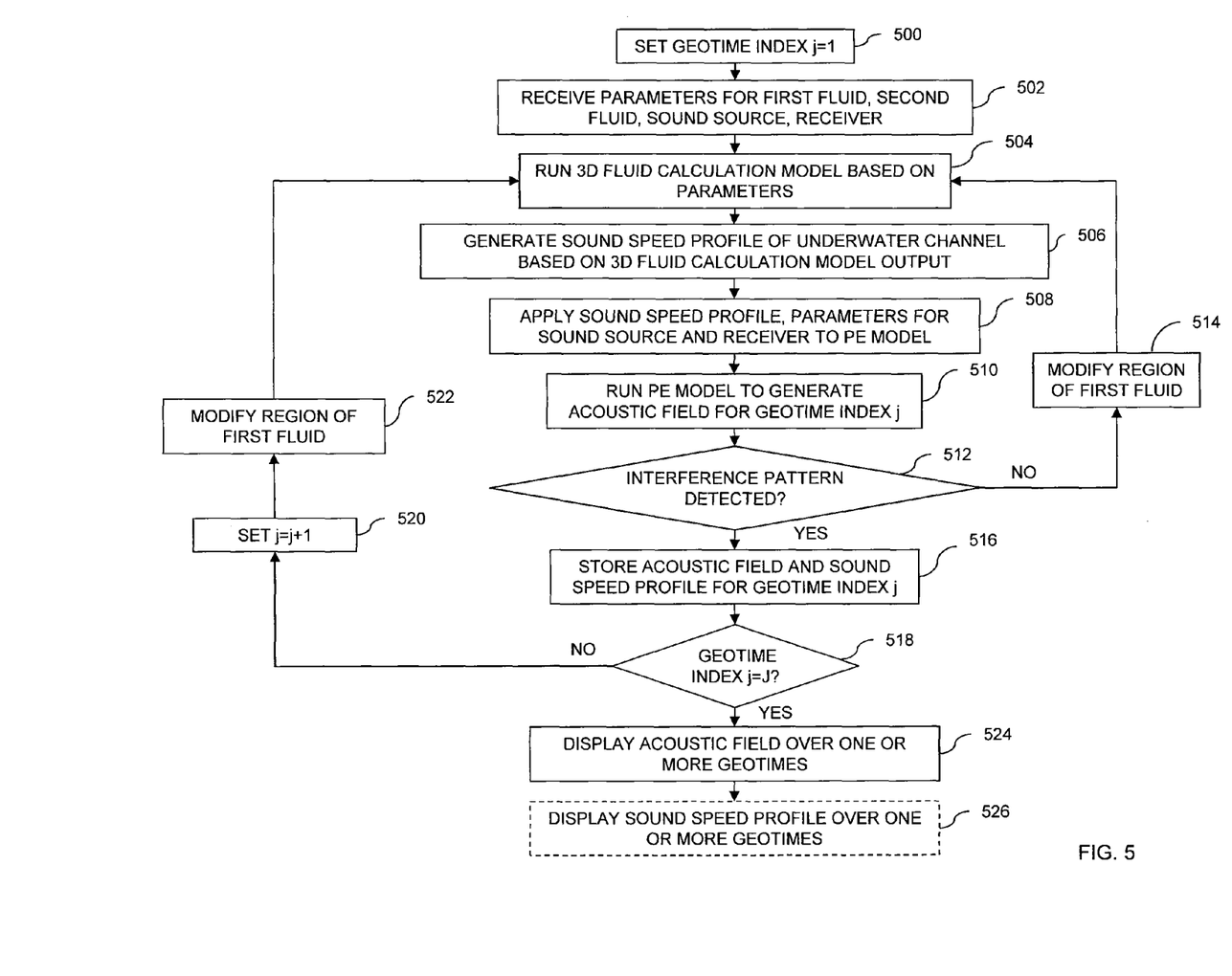
FIG. 5 is a flow chart diagram illustrating an exemplary method for simulating an acoustic field of an underwater channel having a region of fluid within the underwater channel, according to an aspect of the present invention.

Referring next to FIG. 5, an exemplary method for simulating an acoustic field of an underwater channel having a region of fluid (i.e., a first fluid) within fluid (i.e., a second fluid) of the underwater channel is shown. The steps illustrated in FIG. 5 represent an example embodiment of the present invention. It is understood that certain steps may be performed in an order different from what is shown.

At step 500, a geotime index j is set to 1, for example, by controller 108 (FIG. 1). At step 502, parameters may be received for a first fluid (i.e., region 202 (FIG. 4)), a second fluid (i.e., fluid 206), sound source 402 and receiver 404. For example, the parameters may be received from user interface 114 (FIG. 1) and stored in memory 106. In general, a boundary 208 (FIG. 2A) of region 202 may be assumed based on a priori data including, for example, a background fluid velocity in underwater channel 200 (FIG. 2A), an initial shape of region 202, a concentration of fluid 204, and other physical properties of region 202. This information may be translated into a sound speed profile in steps 504 and 506.

At step 504, a 3D fluid calculation model may be processed based on the parameters received in step 502, for example, by 3D fluid calculation model 110 (FIG. 1).

At step 506, a sound speed profile of underwater channel 200 (FIG. 4) having region 202 is generated based on the 3D fluid calculation model output, for example, by sound speed profile generator 102. An example of modeling a fluid shape within an underwater channel and obtaining a sound speed profile for the underwater channel is described further below with respect to FIGS. 6A and 6B.

At step 508, the sound speed profile, and the parameters for sound source 402 (FIG. 4) and receiver 404 are applied to a PE model, for example, PE model 112 (FIG. 1). At step 510, the PE model is processed to generate an acoustic field for geotime index j, for example, by acoustic field generator 104 (FIG. 1).

At step 512, it is determined whether an interference pattern is detected in the generated acoustic field for example, by controller 108 (FIG. 1). If an interference pattern (or a boundary) is not detected, step 512 proceeds to step 514.

In general, steps 504 and 506 generate boundary 208 (FIG. 2A) and the sound speed profile of the region 202 based on a combined oceanographic model (such as ROMS ocean model) and the Lagrangian method. The output of step 506 is a sound speed profile for underwater channel 200 (FIG. 2A) with a position of the region 202 at a fixed geotime. Steps 508 and 510 generate an acoustic field. At step 512, the result of the acoustic field may be checked (for example, using processing tools depending upon receiver 404 (FIG. 4) for detection of boundaries or acoustic field interference patterns).

At step 514, region 202 of fluid 204 (FIG. 2A) is modified, for example, via user interface 114 (FIG. 1). Region 202 (FIG. 2A) may be modified, for example, by changing a shape of region 202, a position of region 202 in underwater channel 200, a physical characteristic of fluid 204 or any combination thereof. Step 514 proceeds to step 504. Steps 504-510 may be repeated until an interference pattern (or a boundary) is detected. For example, if a prescribed condition is not satisfied, then the boundary 208 (FIG. 2A) may change slightly and steps 504-510 may be repeated. A final termination process for the method shown in FIG. 5 may be prescribed by a set of oceanographic conditions that include a level of mixing between the two fluids (fluid 204 and fluid 206 as shown in FIG. 2A) and the position of region 202.

If, at step 512, an interference pattern (or boundary) is detected, step 512 proceeds to step 516.

At step 516, the acoustic field and sound speed profile for geotime index j may be stored, for example, by memory 106 (FIG. 1). In an exemplary embodiment, the parabolic equation may be based on a split-step Fourier algorithm that calculates the acoustic field in spatial and temporal domains.

At step 518, it is determined whether geotime index j is equal to J (where J may be greater than or equal to 1), for example, by controller 108 (FIG. 1). If geotime index j is not equal to J, step 518 proceeds to step 520.

At step 520, geotime index j is set to j+1, for example, by controller 108 (FIG. 1). At step 522, region 202 of fluid 204 (FIG. 2A) is modified, for example, via user interface 114 (FIG. 1). Region 202 (FIG. 2A) may be modified, for example, by changing a shape of region 202, a position of region 202 in underwater channel 200, a physical characteristic of fluid 204 or any combination thereof. Step 522 proceeds to step 504. Steps 504-516 may be repeated until geotime index j is equal to J.

If, at step 518, geotime index j is equal to J, step 518 proceeds to step 524. At step 524, the acoustic field is displayed over one or more geotimes, for example, by display 116 (FIG. 1). At optional step 526, the sound speed profile over one or more geotimes may be displayed, for example, by display 116 (FIG. 1).

Due to present computer speed limitations, an instantaneous model run at this time is typically not possible, as the simulations for the combined movement of the volume of region 202 (FIG. 2A), and the corresponding acoustic field calculation may take up to several hours. However, the processing speed may be improved by the process of using parallel Graphic Processing Units (GPU) instead of existing Central Processing Units (CPU).

Figure 6A:
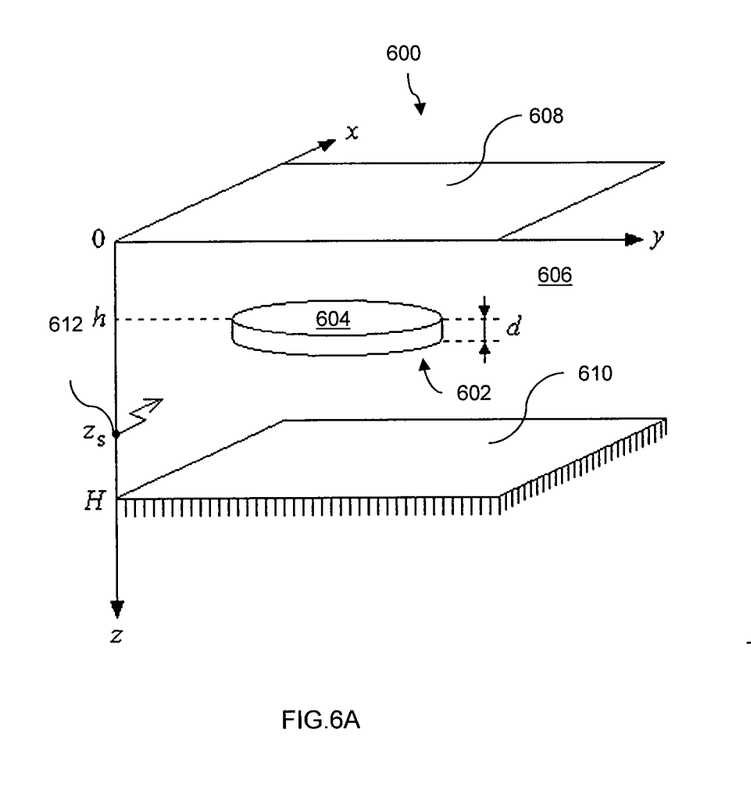
FIG. 6A is a perspective view diagram of a water column having an example modeled region of fluid, according to an aspect of the present invention.
Figure 6B:
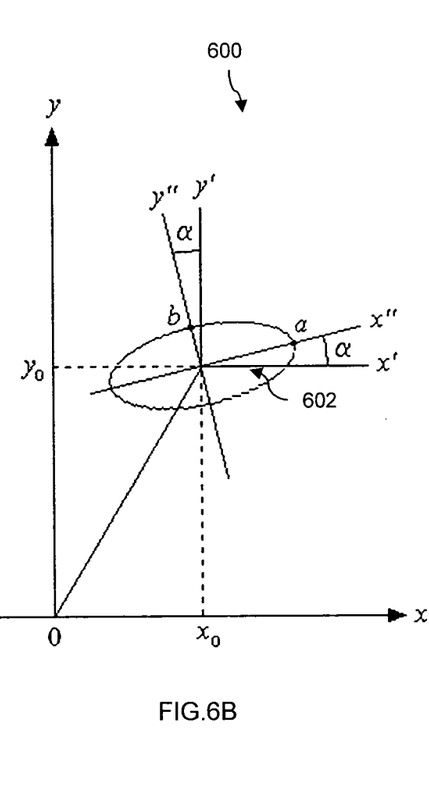
FIG. 6B is a top plan view diagram of the water column shown in FIG. 6A, according to an aspect of the present invention.

Referring next to FIGS. 6A and 6B, an example of obtaining a sound speed profile for modeled region 602 of fluid 604 within fluid 606 of water column 600 is shown. In particular, FIG. 6A is a perspective view diagram of water column 600, in the x, y and z directions; and FIG. 6B is a top plan view diagram of water column 600, in the x-y plane. In FIGS. 6A and 6B, fluid 604 may have a different density than fluid 606.

As shown in FIG. 6A, region 602 is positioned in fluid 606 at a position between top surface 608 and bottom surface 610, where water column 600 has a depth H. Sound source 612 is illustrated as being placed at position $z_s$ at the z-axis. In the description below, a Cartesian coordinate system is assumed. As shown in FIGS. 6A and 6B, region 602 is illustrated as a cylinder having an elliptical shape, for ease in explanation of a relationship between region 602 and calculation of the sound speed profile. Although region 602 as a cylinder having an elliptical shape is described, it is understood that region 602 may be any regular or irregular polygonal shape.

Parameters of water column 600 that may change with geotime may include: a depth h of an upper boundary of region 602, a thickness d of region 602 (where h+d≤H), semi-axes a, b of region 602 (i.e., of the ellipse) (where a≥b), coordinates $x_0$, $y_0$ of a center of region 602 (i.e., of the ellipse) and an angle of rotation α of region 602 (i.e., of the ellipse) (where 0≤α<π).

The canonical equation of an ellipse may be represented as:

$$\frac{x''^2}{a^2} + \frac{y''^2}{b^2} = 1 \quad (1)$$

A connection between coordinate systems in the horizontal plane (i.e., the x-y plane) may be represented as:

$$\begin{cases} x'' = (x - x_0)\cos\alpha + (y - y_0)\sin\alpha \\ y'' = -(x - x_0)\sin\alpha + (y - y_0)\cos\alpha \end{cases} \quad (2)$$

The sound speed profile outside of region 602 may be represented as c(z). The sound speed profile inside of region 602 may be represented as c(z)+Δc. The sound speed profile as a function of three dimensions c(x, y, z) may be represented as:

$$c(x, y, z) = \begin{cases} c(z), & \text{if } \frac{x''^2}{a^2} + \frac{y''^2}{b^2} > 1 \text{ or } z < h \text{ or } z > h+d \\ c(z) + \Delta c, & \text{if } \frac{x''^2}{a^2} + \frac{y''^2}{b^2} \leq 1 \text{ and } h \leq z \leq h+d \end{cases} \quad (3)$$

The above three-dimensional sound speed profile may be used as an input to PE equation model 112 (FIG. 1), for example, to analyze the effect the sound speed profile may have on the acoustic field.

Figure 7A:
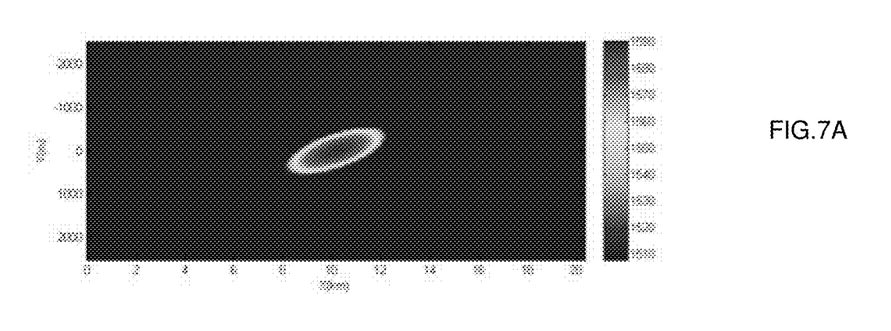
FIGS. 7A and 7B are images of an example sound speed profile of an idealized volume of an oil patch inside a three-dimensional (3D) waveguide in the X-Y plane and the X-Z plane, respectively, according to an aspect of the present invention.
Figure 7B:
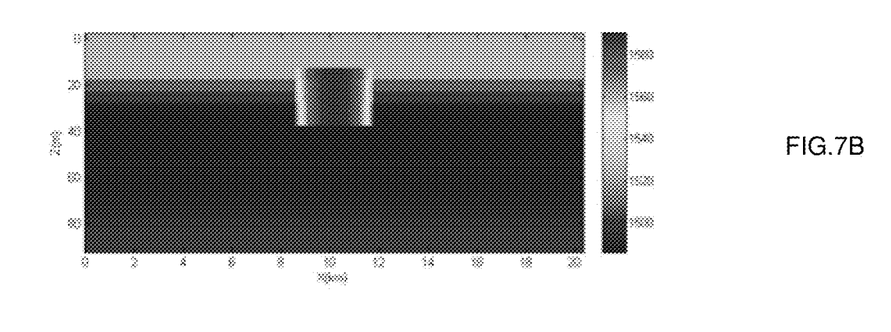

Referring next to FIGS. 7A-9E, an example of simulating an acoustic field for an idealized volume of an oil patch inside a 3D waveguide is shown. Results are provided for two different geotimes. In particular, FIG. 7A is an image of a sound speed profile of the idealized volume in the X-Y plane; FIG. 7B is an image of the sound speed profile of the idealized volume in the X-Z plane; FIG. 8A is an image of the acoustic field of the waveguide having the oil patch in the X-Y plane as a function of pressure at the bottom of the X-Y plane; FIG. 8B is an image of the acoustic field in the X-Y plane as a function of intensity; FIG. 8C is an image of the acoustic field in the X-Z plane as a function of pressure at a center of the X-Z plane; FIG. 8D is an image of the acoustic field in the vicinity of a horizontal line array (HLA) as a function of depth and geotime; and FIG. 8E is an image of the acoustic field in the vicinity of a vertical line array (VLA) as a function of distance and geotime. FIGS. 8A-8E represent simulation results for a first geotime. FIGS. 9A-9E are similar to FIGS. 8A-8E, except the simulation results are for a different geotime where a shape of the oil patch has changed. In FIGS. 7A-9E, color corresponds to the intensity of acoustic field as defined by the color key to the right of each figure.

FIGS. 7A-8E show a 3D waveguide calculation when a sound source is placed at an x,y,z position (0 km, 0 km, 50 m) in a 3D waveguide with dimensions (X=20 km, Y=3 km, Z=100 m). A patch of oil with dimensions (x=3 km, y=2 km, z=20 m) is pulsating inside the waveguide while the sound source is emitting sound at a monotone frequency of 300 Hz. In FIGS. 7A and 7B, the concentration of the material inside of the patch is considered at the center, and gradually tapers off at the edges (dimensions of the patch is to the scale with the waveguide dimensions).

Figure 8A:
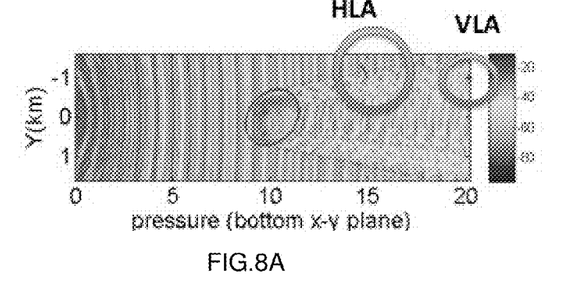
FIGS. 8A, 8B and 8C are images of an example acoustic field (i.e., pressure and intensity) in the X-Y plane and the X-Z plane as a function of horizontal and vertical distance in X-Y-Z coordinates respectively, for the oil patch inside the 3D waveguide shown in FIGS. 7A and 7B, according to an aspect of the present invention.
Figure 8B:
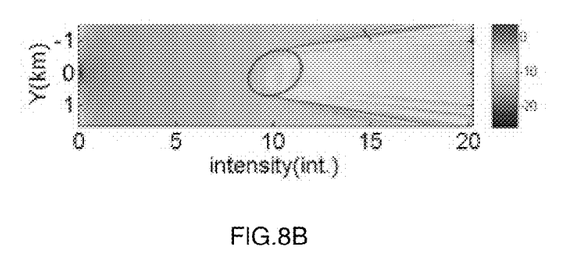
Figure 8C:
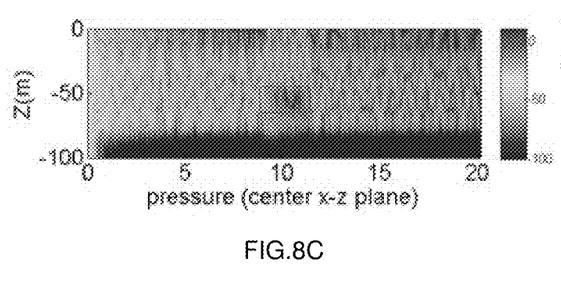
Figure 8D:
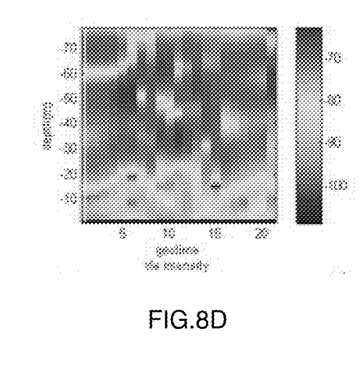
FIGS. 8D and 8E are example images of acoustic intensity calculated versus depth and distance as a function of geotime for a horizontal receiver array (HLA) and a vertical receiver array (VLA), respectively, positioned as shown in FIG. 8A.
Figure 8E:
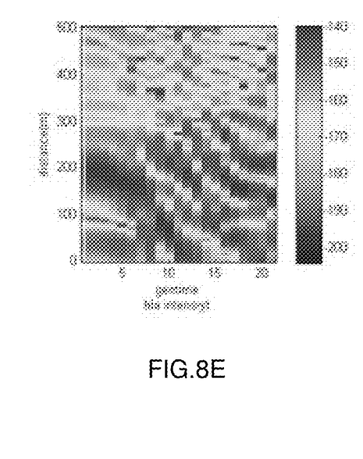

The acoustic field before and after it hits the oil patch is considered for further examination. Modal calculation shows a drastic change in the modal energy distribution inside the water column due to the existence of the fluid inclusion. As shown in FIG. 8A, fringe patterns are observed around the edges of the inclusion, depicting that the horizontal Lloyd's mirror effect is changing as a function of the boundary movement in geotime, Tg. This feature is related to the oceanographic changes occurring in the water column.

Figure 9A:
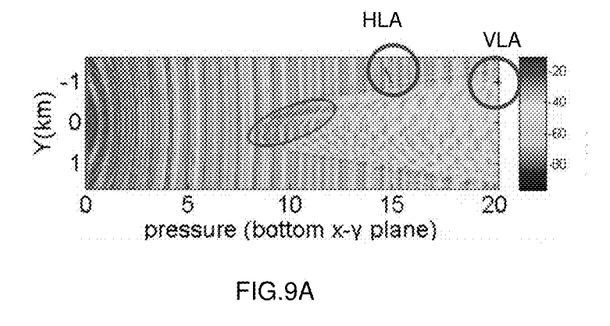
FIGS. 9A, 9B and 9C are images of an example acoustic field (i.e., pressure and intensity) in the X-Y plane and the X-Z plane as a function of horizontal and vertical distance in X-Y-Z coordinates respectively, for the oil patch inside the 3D waveguide shown in FIGS. 7A and 7B, at a different geotime than shown in FIGS. 8A, 8B and 8C, according to an aspect of the present invention.
Figure 9B:
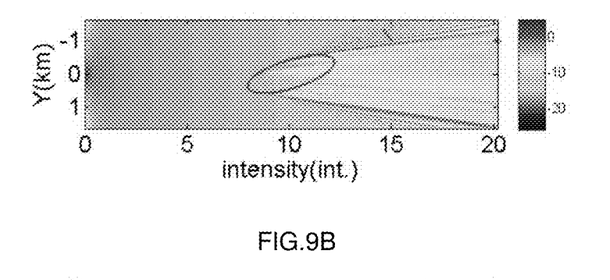
Figure 9C:
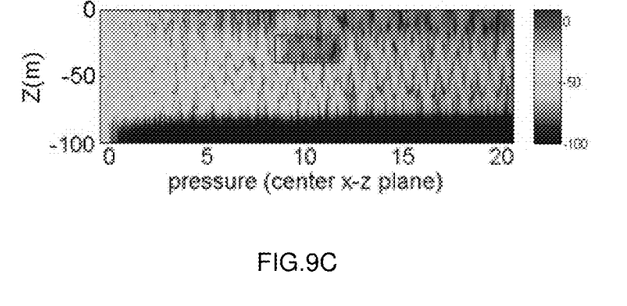
Figure 9D:
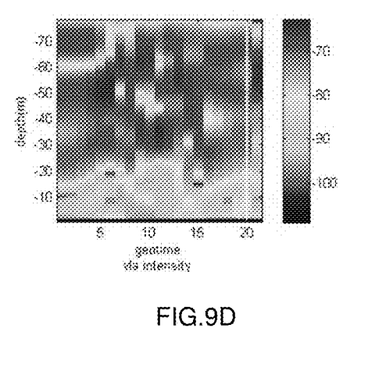
FIGS. 9D and 9E are example images of acoustic intensity calculated versus depth and distance as a function of geotime for a horizontal receiver array (HLA) and a vertical receiver array (VLA), respectively, positioned as shown in FIG. 9A for the different geotime of FIG. 9A, according to an aspect of the present invention.
Figure 9E:
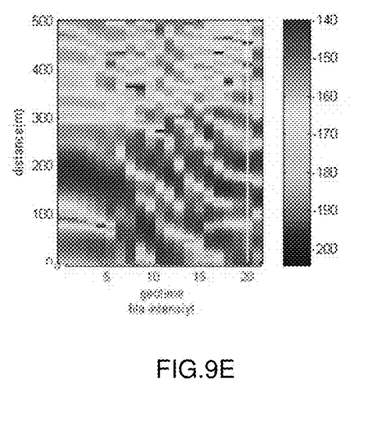

FIGS. 9A-9D are simulation results for a different geotime. As shown in FIGS. 9A and 9B, the shape of the oil patch and its dimensions, as well as its position within the water column has changed as compared with FIGS. 8A and 8B.

The example acoustic fields described with respect to FIGS. 7A-9E are calculated by using realistic values for the sound speed measurement in oil using the elliptically-shaped oil spill volume mentioned above. The sound speed profile for the waveguide as well as the acoustic field in the waveguide calculated for different spatial and temporal instances of the oil patch in the oil patch volume are shown in FIG. 7A-9E. The oil patch volume is moving up and down and its boundaries are changing in geotime. FIGS. 7A and 7B show the sound speed profile at a fixed geotime. FIGS. 8A-8C and FIGS. 9A-9C indicate two different geotime instances of the waveguide where the oil patch has moved in the waveguide. FIGS. 8D, 8E, 9D and 9E show the acoustic field on a vertical (VLA) and horizontal (HLA) arrays respectively for two different geotimes. The positions of these arrays are indicated in respective FIGS. 8A and 9A. FIGS. 8A-9E show that the acoustic field is drastically changed when the oil patch is in a different position in the water column. The fringes observed in the acoustic intensity across the VLA and HLA may be used as representative diagnostic tools for detecting the boundaries of the oil volume patch. For example, related patent application entitled "METHOD FOR DETECTION OF A PLUME OF A FIRST FLUID WITHIN A SECOND FLUID" describes methods for detecting a velocity and physical characteristics of a plume of fluid from the interference pattern measured at the receiver.

Although the invention has been described in terms of methods and simulators for simulating an acoustic field of an acoustic waveguide having a region of a first fluid within a second fluid, it is contemplated that one or more steps and/or components may be implemented in software for use with microprocessors/general purpose computers (not shown). In this embodiment, one or more of the functions of the various components and/or steps described above may be implemented in software that controls a computer. The software may be embodied in non-transitory tangible computer readable media (such as, by way of non-limiting example, a magnetic disk, optical disk, hard drive, etc.) for execution by the computer.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for simulating an acoustic field of an acoustic waveguide, the method comprising:

generating, by a processor, a sound speed profile of the acoustic waveguide, the acoustic waveguide having a region of a first fluid within a second fluid, the region of the first fluid including a volume of the first fluid, the first fluid having a different acoustic index of refraction than the second fluid;

applying the sound speed profile and predetermined parameters of a sound source and a receiver to a parabolic equation (PE) model of sound propagation in the acoustic waveguide; and determining, by the processor, the acoustic field of the acoustic waveguide from the PE model, such that the acoustic field includes an interference pattern from interference between an acoustic signal of the acoustic source and at least one signal refracted by the region of the first fluid.

2. The method according to claim 1, wherein the acoustic field represents the acoustic waveguide for a first geotime and the method further includes:

changing at least one of a position or a shape of the region of the first fluid within the second fluid to represent the acoustic waveguide for a second geotime;

modifying the sound speed profile based on the changing of the region to form a modified sound speed profile; and repeating the applying of the sound speed profile and the determining of the acoustic field for the modified sound speed profile to form a further acoustic field for the second geotime.

3. The method according to claim 2, the method further including:

displaying at least one of the acoustic field or the further acoustic field.

4. The method according to claim 1, wherein the interference pattern indicates a boundary between the region of the first fluid and the second fluid.

5. The method according to claim 1, wherein the acoustic field is determined in three-dimensions.

6. The method according to claim 1, wherein the first fluid includes at least one of an internal wave, a temperature front or an oceanographic feature with a sound speed different from a sound speed of the second fluid.

7. The method according to claim 1, wherein the generating of the sound speed profile includes:

determining a first sound speed profile representing the region of the first fluid based on a physical characteristic of the first fluid;

determining a second sound speed profile representing the second fluid based on a physical characteristic of the second fluid; and combining the first sound speed profile and the second sound speed profile to form the sound speed profile of the acoustic waveguide.

8. The method according to claim 7, wherein the physical characteristic of each of the first fluid and the second fluid includes at least one of a salinity, a viscosity or a temperature.

9. The method according to claim 1, the method further comprising:

generating a three-dimensional (3D) fluid calculation model of the acoustic waveguide based on at least one of the first fluid, the second fluid, the sound source or the receiver, the 3D fluid calculation model being used to generate the sound speed profile of the acoustic waveguide.

10. The method according to claim 9, wherein the 3D fluid calculation model uses a regional ocean model system (ROMS) to model the second fluid and a Lagrangian method to model the region of the first fluid.

11. The method according to claim 1, the method comprising, prior to generating the sound speed profile, modeling a boundary between the region of the first fluid and the second fluid.

12. The method according to claim 1, wherein the PE model includes at least one of a parallelized three-dimensional (3D) PE model or a two-way PE model.

13. A simulator for simulating an acoustic field of an acoustic waveguide comprising:

a memory;

a sound speed profile generator, including a processor configured by functions stored in the memory, configured to generate a sound speed profile of the acoustic waveguide, the acoustic waveguide having a region of a first fluid within a second fluid, the region of the first fluid including a volume of the first fluid, the first fluid having a different acoustic index of refraction than the second fluid; and an acoustic field generator, including the processor, configured to:

apply the sound speed profile and predetermined parameters of a sound source and a receiver to a parabolic equation (PE) model of sound propagation in the acoustic waveguide, and determine the acoustic field of the acoustic waveguide from the PE model, such that the acoustic field includes an interference pattern from interference between an acoustic signal of the acoustic source and at least one signal refracted by the region of the first fluid.

14. The simulator according to claim 13, wherein the memory is configured to store at least one of a physical characteristic of the first fluid, a physical characteristic of the second fluid, a shape of the region, a position of the region, the predetermined parameters of the sound source and the receiver, the sound speed profile or the acoustic field.

15. The simulator according to claim 13, further comprising a user interface configured to receive an indication for at least one of a physical characteristic of the first fluid, a physical characteristic of the second fluid, a shape of the region, a position of the region, or the predetermined parameters of the sound source and the receiver.

16. The simulator according to claim 13, wherein the acoustic field represents the acoustic waveguide for a first geotime and the simulator is configured to change at least one of a position or a shape of the region of the first fluid within the second fluid to represent the acoustic waveguide for a second geotime and to determine a further acoustic field for the second geotime.

17. The simulator according to claim 16, further comprising a display configured to display at least one of the sound speed profile, the acoustic field or the further acoustic field.

18. The simulator according to claim 13, wherein the sound speed profile generator is configured to generate the sound speed profile based on a physical characteristic the first fluid and a physical characteristic of the second fluid.

19. The simulator according to claim 18, wherein the physical characteristic of each of the first fluid and the second fluid includes at least one of a salinity, a viscosity or a temperature.

20. The simulator according to claim 13, wherein the first fluid includes at least one of an internal wave, a temperature front or an oceanographic feature with a sound speed different from a sound speed of the second fluid.

21. The simulator according to claim 13, wherein the receiver includes at least one of a vertical line array or a horizontal line array.

22. The simulator according to claim 13, wherein the sound speed profile generator is configured to generate the sound speed profile of the acoustic waveguide using a three-dimensional (3D) fluid calculation model of the acoustic waveguide.

* * * * *